US010552396B2

(12) United States Patent
Dwire et al.

(10) Patent No.: US 10,552,396 B2
(45) Date of Patent: Feb. 4, 2020

(54) MINIMIZE GARBAGE COLLECTION IN HL7 MANIPULATION

(71) Applicant: Health Catalyst, Inc., Salt Lake City, UT (US)

(72) Inventors: Steven E. Dwire, Lawrenceville, GA (US); Hong Gao, Alpharetta, GA (US); Sarika Kandaprabhu, Milton, GA (US); Michael Godinez, Acworth, GA (US); Hassan Khan, Alpharetta, GA (US)

(73) Assignee: Health Catalyst, Inc., Salt Lake City, UT (US)

( * ) Notice: Subject to any disclaimer, the term of this patent is extended or adjusted under 35 U.S.C. 154(b) by 333 days.

(21) Appl. No.: 15/471,903

(22) Filed: Mar. 28, 2017

(65) Prior Publication Data

US 2017/0277733 A1 Sep. 28, 2017

Related U.S. Application Data

(60) Provisional application No. 62/314,043, filed on Mar. 28, 2016.

(51) Int. Cl.
*G06F 16/22* (2019.01)
*G06F 19/00* (2018.01)

(52) U.S. Cl.
CPC ...... *G06F 16/2228* (2019.01); *G06F 19/3418* (2013.01)

(58) Field of Classification Search
CPC .......................... G06F 16/2228; G06F 19/3418
USPC ........................................................ 707/741
See application file for complete search history.

(56) References Cited

U.S. PATENT DOCUMENTS 7,844,957 B2 * 11/2010 Doucette ............... G06F 8/30
717/105

OTHER PUBLICATIONS

HAPI Project, "HAPI—The Open Source HL7 API for Java," May 12, 2014 (available at: http://hl7api.sourceforge.net/index.html).
Mirth Connect, "User Guide," Oct. 16, 2015 (available at: http://www.mirthcorp.com/community/wiki/display/mirth/User+Guide).
Oracle, "Class StringTokenizer," Java SE 7, Jul. 7, 2011 (available at: http://docs.oracle.com/javase/7/docs/api/java/util/StringTokenizer.html#nextToken)).

(Continued)

*Primary Examiner* — Robert W Beausoliel, Jr.
*Assistant Examiner* — Arthur Ganger
(74) *Attorney, Agent, or Firm* — Patent Law Works LLP (57) ABSTRACT

Disclosed are a system and method for processing HL7 messages. A method includes receiving, an HL7 message; storing the HL7 message in a memory; creating a data structure representation of the stored HL7 message in the memory that stores a start index and an end index of the stored HL7 message, wherein the start index indicates a beginning of the stored HL7 message and the end index indicates an end of the stored HL7 message; hierarchically creating, from the data structure representation of the stored HL7 message, one or more data structure representations in the memory that store at least one start index and at least one end index corresponding to one or more fragments in the stored HL7 message; and, modifying the stored HL7 message according to the at least one start index and a corresponding end index of the fragments in the HL7 message.

20 Claims, 6 Drawing Sheets

(56) References Cited

OTHER PUBLICATIONS

Williams, Michael J., "Java Garbage Collection Basics," Mar. 12, 2015 (available at: https://web.archive.org/web/20150312191945/http://www.oracle.com/webfolder/technetwork/tutorials/obe/java/gc01/index.html).

Panwar, Abhijeet, "How String object is garbage collected in java?" StackOverflow.com, Jul. 12, 2014 (available at: http://stackoverflow.com/questions/24711100/how-string-object-is-garbage-collected-in-java).

Corepoint Health, "HL7 ADT—Admit Discharge Transfer," Nov. 16, 2015 (available at: https://www.corepointhealth.com/resource-center/hl7-resources/hl7-adt).

Kim, et al. "Integration of IEEE 1451 and HL7 Exchanging Information for Patients' Sensor Data," *Journal of Medical Systems*, vol. 34, pp. 1033-1041 (Jun. 17, 2009).

Health Level Seven International, "About HL7," Nov. 16, 2015 (available at: http://www.hl7.org/about/index.cfm?ref=common).

Balachandran, Mohan, "HL7 201—The Admission, Discharge, Transfer (ADT) Message," 2015 Healthcare Innovation Report: 4 Big Ideas (Feb. 15, 2014).

Health Level Seven International, "HL7 Version 2.5.1 Implementation Guide: Birth and Fetal Death Reporting, Release 1—US Realm; DSTU Release 1.1," Feb. 2015.

Health Level Seven International, "HL7 Version 2.5.1—Chapter 2: Control" Apr. 2007.

\* cited by examiner

Sample HL7 Message

```
MSH|^~\&|XRAY||CDB||200006021411||ORU^R01|K172|P|
PID||10535^van Beethoven&van^Ludwig^A^III^Dr^PHD^^^&MPI.Community Health and
Hospitals&L^L^3^M10^MR^& Good Health Hospital.Community Health and Hospitals&L^A|
OBR|1|X89-1501^OE|78912^RD|71020^CHEST XRAY AP \T\ LATERAL|||19873290800||||F|
OBX|1|CE|71020&IMP^RADIOLOGIST'S IMPRESSION|4|^MASS LEFT LOWER LOBE|||A|||F|
OBX|2|FT|71020&GDT|1|circular density (2 x 2 cm) is seen in the posterior segment of the LLL.~A
second, less well-defined infiltrated circulation density is seen in~the R mid lung field and
appears to cross the minor fissure#|||||F|
```

Segment object:
- rawHL7: a reference to the above block
- startIndex: 50 (the beginning of the second line)
- endIndex: 208 (the end of the second line)
- childFragments: a list of the following HL7Fragment-inherited objects, in order:

Field object:
- rawHL7: a reference to the above block
- startIndex: 54 (the start of the first field – skipping the segment name, PID)
- endIndex: 54 (the end of the first field – because the first field is empty)
- childFragments: null (the field has not yet been further parsed into repetitions)

Field object:
- rawHL7: a reference to the above block
- startIndex: 56 (the start of the second field – skipping the field separator)
- endIndex: 207 (the end of the second field – including all components and subcomponents)
- childFragments: null (the field has not yet been further parsed into repetitions)

FIG. 5

FIG. 6 ial Application No. 62/314,043, filed on Mar. 28, 2016, which is hereby incorporated by reference in its entirety.

MINIMIZE GARBAGE COLLECTION IN HL7 MANIPULATION

CROSS-REFERENCE TO RELATED APPLICATIONS

This application claims the benefit of U.S. Provisional Application No. 62/314,043, filed on Mar. 28, 2016, which is hereby incorporated by reference in its entirety.

BACKGROUND

Health Level-7 or HL7 refers to international standards for transfer of data between software applications used by various healthcare providers. These different providers may operate disparate computer systems to process, share, and organize the different data. It is desirable that these computer systems interface with each other allowing transfer of data between the different computing systems. HL7 is a standard that enables such communication between the computer systems. In healthcare data processing, having computing devices that efficiently work with HL7 messages is extremely valuable.

SUMMARY

One embodiment of the disclosure provides a method for processing HL7 messages, comprising: receiving, over an electronic data network, an HL7 message and storing the HL7 message in a memory as a stored HL7 message; creating a data structure representation of the stored HL7 message in the memory that stores a start index of the stored HL7 message and an end index of the stored HL7 message, wherein the start index of the stored HL7 message indicates a beginning of the stored HL7 message and the end index of the stored HL7 message indicates an end of the stored HL7 message; hierarchically creating, from the data structure representation of the stored HL7 message, one or more data structure representations in the memory that store at least one start index and at least one end index corresponding to one or more fragments in the stored HL7 message; and, modifying the stored HL7 message according to the at least one start index and a corresponding end index of the fragments in the HL7 message.

Another embodiment of the disclosure provides a computing device for processing HL7 messages. The computing device comprises a processor and a memory with instructions stored thereon, such that when the processor executes the instructions, the device is configured to: receive, over an electronic data network, an HL7 message and store the HL7 message in the memory as a stored HL7 message; hierarchically create one or more data structure representations in the memory that store at least a start index and an end index of fragments in the stored HL7 message, wherein the stored HL7 message comprises fragments organized by type in a hierarchical manner, and wherein the hierarchical manner indicates that the stored HL7 message comprises one or more segments, each segment comprising one or more fields, each field comprising one or more repetitions, each repetition comprising one or more components, and each component comprising one or more subcomponents; and, modify the stored HL7 message according to at least one start index and a corresponding end index of the fragments in the stored HL7 message.

Yet another embodiment of the disclosure provides a non-transitory computer readable medium for processing HL7 messages, the non-transitory computer readable medium containing program instructions that causes a computer to perform the method comprising: receiving, over an electronic data network, an HL7 message and storing the HL7 message in a memory as a stored HL7 message; hierarchically creating one or more data structure representations in the memory that store at least a start index and an end index of fragments in the stored HL7 message, wherein a start index indicates the beginning of a fragment and an end index indicates the end of a fragment, wherein the stored HL7 message comprises fragments organized by type in a hierarchical manner, and wherein the hierarchical manner indicates that an stored HL7 message comprises one or more segments, each segment comprising one or more fields, each field comprising one or more repetitions, each repetition comprising one or more components, and each component comprising one or more subcomponents; and, modify the stored HL7 message according to at least one start index and a corresponding end index of the fragments in the stored HL7 message.

DETAILED DESCRIPTION

Embodiments of the disclosure provide a method and system to process an HL7 message. Healthcare information is often communicated between computer systems from different vendors using a loosely-defined industry-standard format called HL7. HL7 defines the general structure and semantics of communication, but often leaves details of the communication to the discretion of different vendors. Mitigating differing interpretations or applications of the standard often requires reorganizing or adjusting the contents of HL7 messages received from one vendor before they are transmitted to another vendor. Therefore, efficient methods of manipulating HL7 messages (i.e., use of transformations) on computing systems are valuable.

HL7 messages describe healthcare events in a hierarchical manner, with a single message composed of multiple segments. Each segment is composed of multiple fields. Each field may have zero or more repetitions. Each repetition may have multiple components, and each component may have multiple subcomponents.

Embodiments of the disclosure provide a method of using indices to mark fragments of an HL7 message. When a software client is working with or manipulating the HL7 message, the software client may change the original message by modifying certain values in the fragments of interest and updating the indices of the fragments accordingly. This method works directly with the original HL7 message and thus, avoids making multiple copies of the HL7 message. By adopting certain aspects of the disclosure, a software system may manipulate HL7 messages without consuming too much RAM or necessitating the need for a computer to spend a long amount of time in "garbage collection," thereby improving the functioning of the computer itself. "Garbage collection" is a memory management process where a memory management program attempts to reclaim memory occupied by objects that are no longer in use by a currently running program. In conventional approaches, unnecessary pressure is placed on a computer runtime system, since HL7 message processing may involve multiple copies of values within the hierarchy stored in memory. As such, computer resources would be diverted to garbage collection where no-longer-used memory blocks are rearranged and cleaned up so that they become available for future productive work. During "garbage collection" time, the throughput of an HL7 message processing system is significantly reduced. In some instances, the throughput is measured in terms of number of HL7 messages processed per second. Embodiments of the disclosure provide an efficient system and method for HL7 message processing, allowing throughput to remain high. Accordingly, embodiments of the disclosure provide systems and method that improve the functioning of the computer itself by reducing and streamlining memory usage.

Figure 1:
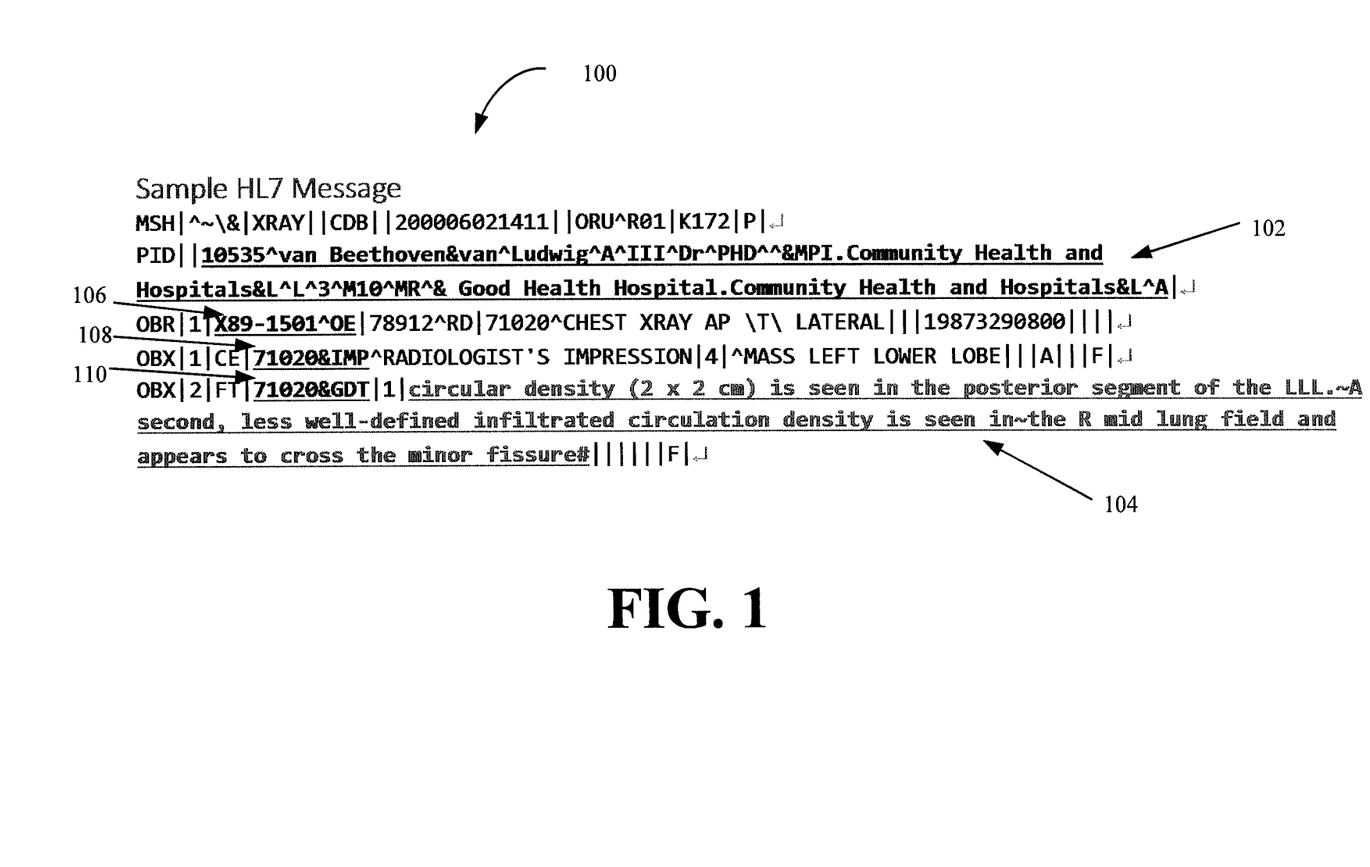
FIG. 1 is a sample HL7 message, in accordance with some embodiments of the disclosure.

FIG. 1 provides an example of an HL7 message, according to one embodiment of the disclosure. The HL7 hierarchical message structure contains multiple separators or delimiters. Segments are often separated by carriage returns "↵", and fields are often separated by a pipe character "|" (note, the pipe character may also separate the segment ID from the first data field in each segment). Repetitions are often separated by tilde character "~". Components are often separated by a hat character "^". Subcomponents are often separated by an ampersand character "&". Usually when there are no subcomponents, the ampersand may be omitted. The delimiters used for each separation in the hierarchy may follow the sample convention provided or may follow a different convention using other symbols. Thus, in one embodiment, the object hierarchy used to interpret HL7 messages is message, segment, field, repetition, component, and subcomponent.

For example, in FIG. 1, the message 100 is composed of multiple segments with segment labels or segment IDs MSH, PID, OBR, OBX, and OBX. These labels are known identifiers in HL7. In FIG. 1, underlines are used to highlight several features, but the underlines are not part of the message. The underlined item 102 provides an example of a complex field with multiple components and subcomponents. The underlined item 104 highlights a field with repetitions. The underlined item 106 highlights a field with components. The underlined items 108 and 110 highlight components with subcomponents. FIG. 1 is an example illustrating the syntax and hierarchical structure of an HL7 message. The defining delimiters and separators may be modified from one HL7 standard to another, but as long as the hierarchical structure is preserved, embodiments of the disclosure may be applied to each HL7 message.

Figure 2:
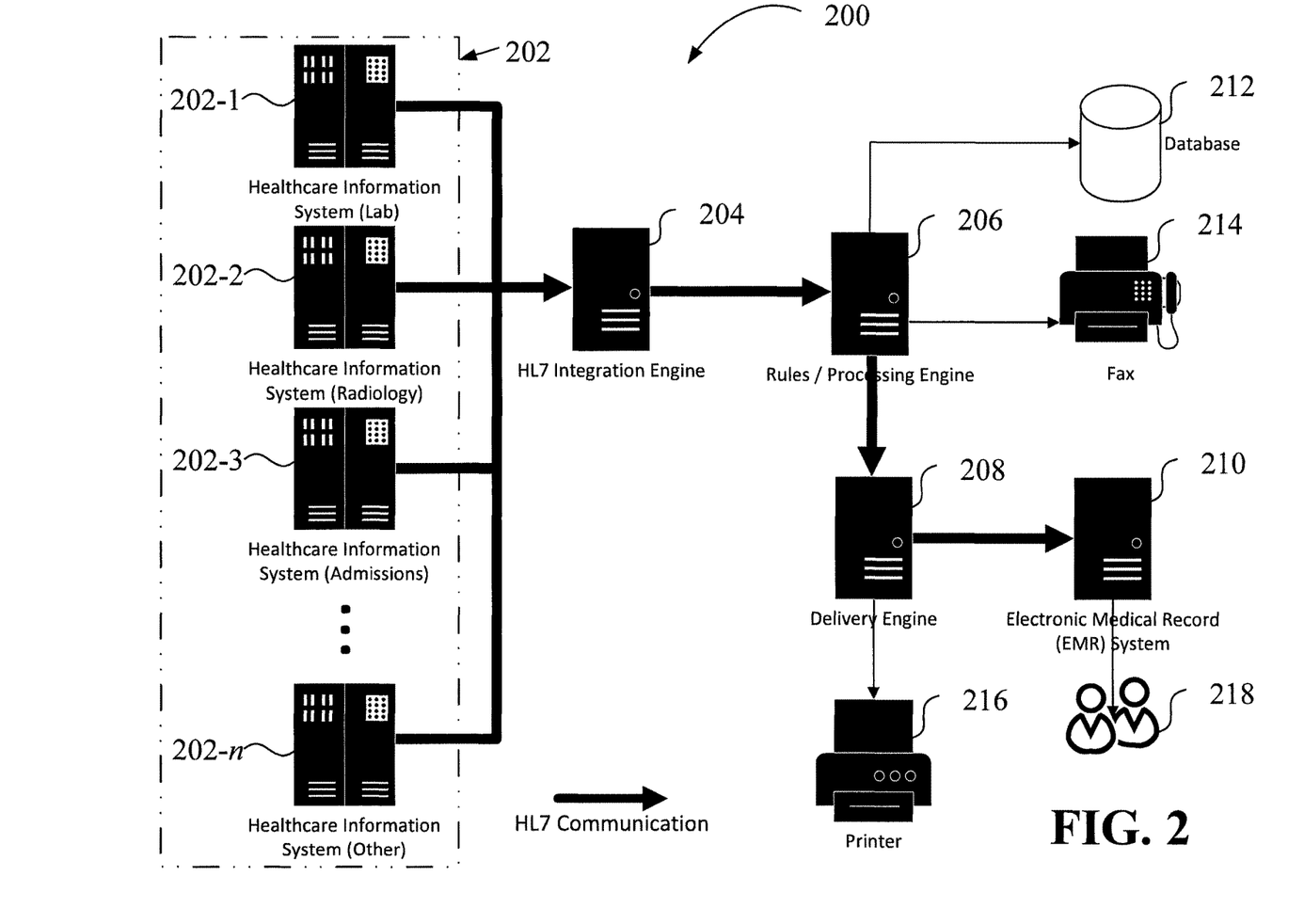
FIG. 2 is an example of a schematic illustrating an overview of a system for the flow of HL7 communication, in accordance with some embodiments of the disclosure.

FIG. 2 is a schematic illustrating an overview of an example system 200 for the flow of HL7 communication. The Healthcare Information Systems 202-1 to 202-*n* represent different computing environments that may receive and send HL7 messages over an electronic data network, such as the Internet. In the current embodiment, a HL7 Integration Engine 204 receives HL7 messages from one or more of the Healthcare Information Systems 202-1 to 202-*n*. For simplicity in description, the reference number 202 is used herein to refer to at least one of the Healthcare Information Systems 202-1 to 202-*n*. The HL7 Integration Engine 204 may send HL7 messages to the Rules/Processing Engine 206. In turn, the Rules/Processing Engine 206 may send HL7 messages to the Delivery Engine 208, which in turn may send HL7 messages to the Electronic Medical Record (EMR) System 210.

Health Information Systems 202 are each represented with a mainframe computer symbol, and the HL7 Integration Engine 204, Rules/Processing Engine 206, Delivery Engine 208, and EMR 210 are represented with a server symbol. Each of the mainframes and servers are computer devices with non-transitory computer readable media and one or more processors. In some implementations, these different computing systems may comprise multiple computer devices networked to perform as a single unit, i.e., a server symbol in FIG. 2 may represent multiple servers linked to realize a prescribed functionality. Is some embodiments, one or more of the HL7 Integration Engine 204, the Rules/Processing Engine 206, and the Delivery Engine 208 may be embodied on a single computing device.

The example system 200 may also include devices not compatible with HL7, for example, a fax machine 214, a printer 216, etc. In some instances, the different computing devices are coupled to one or more databases. In FIG. 2, the Rules/Processing Engine 206 is connected to Database 212. The mainframes and servers represented in FIG. 2 may receive, manipulate, and send HL7 messages. Thus, embodiments of the disclosure may be applied at any healthcare computing device in the architecture representation of FIG. 2 for processing HL7 messages.

Figure 3:
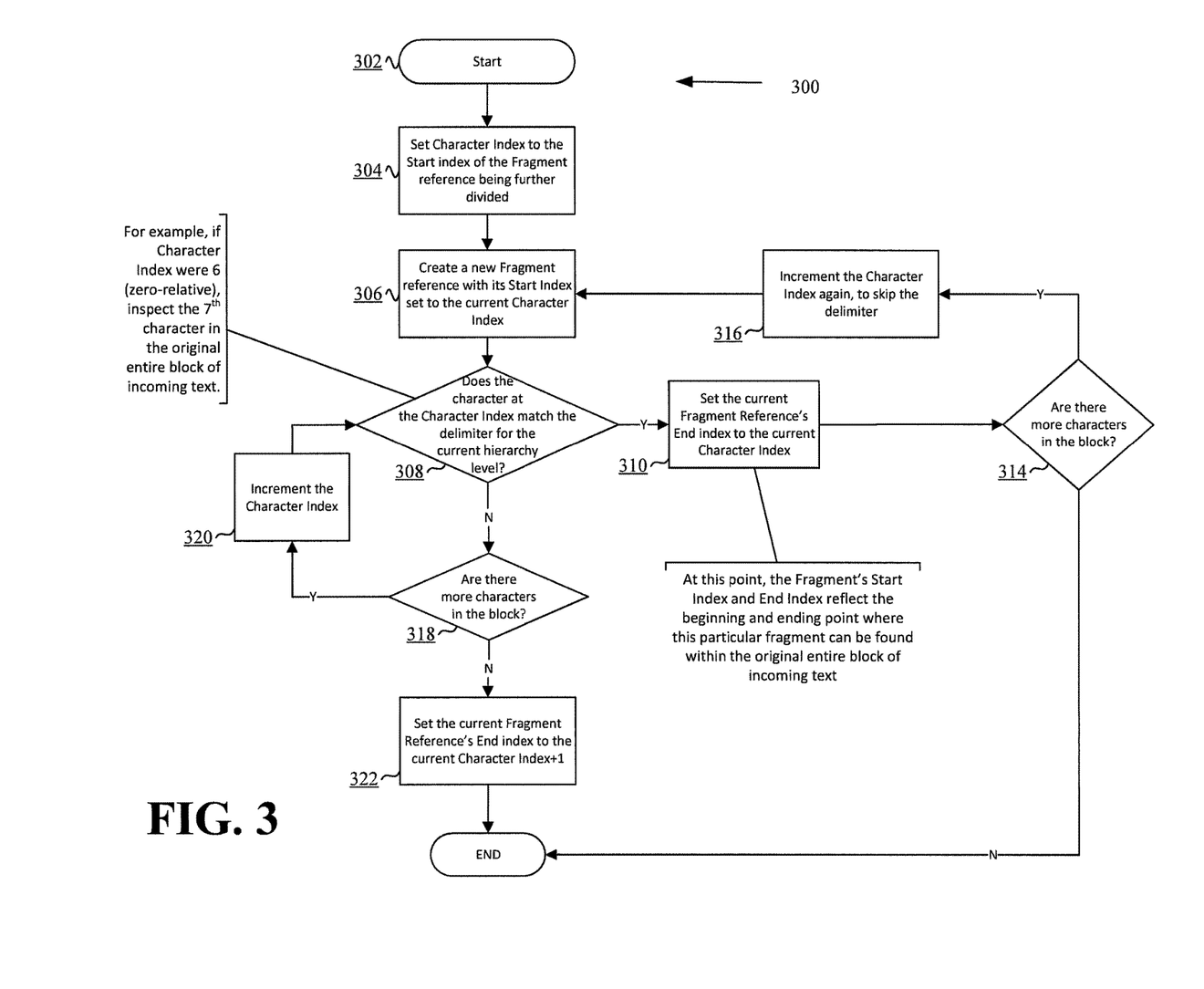
FIG. 3 is an example flow diagram to identify HL7 message features, in accordance with some embodiments of the disclosure.

FIG. 3 provides an example flow diagram to identify HL7 message features, in accordance with some embodiments of the disclosure. The process 300 illustrated in the flow diagram of FIG. 3 relies on the hierarchical structure of an HL7 message. In some embodiments, when a computing device receives an HL7 message through its network interface, the computing device stores the HL7 message in its working memory, e.g., random access memory (RAM). The computing device then creates one or more fragment objects for the received HL7 message.

A fragment object is a data structure stored in the working memory or another storage medium, such as a solid-state hard drive or magnetic hard drive. A fragment object may track several properties of the received HL7 message illustrated below as 1 to 6. A fragment object may track the entire HL7 message or a portion or part of the HL7 message, such as a segment, field, repetition, component, or subcomponent.

1. The fragment object may include a property called "rawHL7", which holds the HL7 message in a "String" format. In some embodiments of the disclosure, the "rawHL7" property is a reference to a memory location in RAM where the HL7 message is stored.

2. The fragment object may include a property called "startIndex", which holds an index of the first character in "rawHL7" that represents content for a specific HL7 fragment.

3. The fragment object may include a property called "endIndex", which holds an index just beyond the last character in "rawHL7" that represents content for a specific HL7 fragment. In some embodiments, the "endIndex" may be engineered to hold an index of the last character for the specific HL7 fragment.

4. The fragment object may include a property called "childFragments", which are ordered list of HL7 fragments.

5. The fragment object may include a property called "hasChangedChildren", which indicates whether a software client has requested a change to any value held in any of the HL7 fragments in the "childFragments" list.

6. The fragment object may include a property called "parentFragment". Thus, when an HL7 fragment is added to another HL7 fragment's "childFragments" collection, the added fragment's "parentFragment" is set to reference the HL7 fragment to which it was added.

In addition to the previous properties, fragment objects that are segments, i.e., segment objects, may have additional properties. For example, a segment may be a required segment in an HL7 message, and as such, a Boolean property "RequiredSegment" may be defined in the segment object signifying whether this segment object is required. Additionally, a segment object may include a Boolean property called "ghostParent" which indicates whether the current segment is a "ghost parent". The "ghostParent" is set to true if a child segment has a non-required parent segment missing in the original message. Lastly, the segment object may include a property called "Segments" which is an ordered list of child segments.

Figure 4:
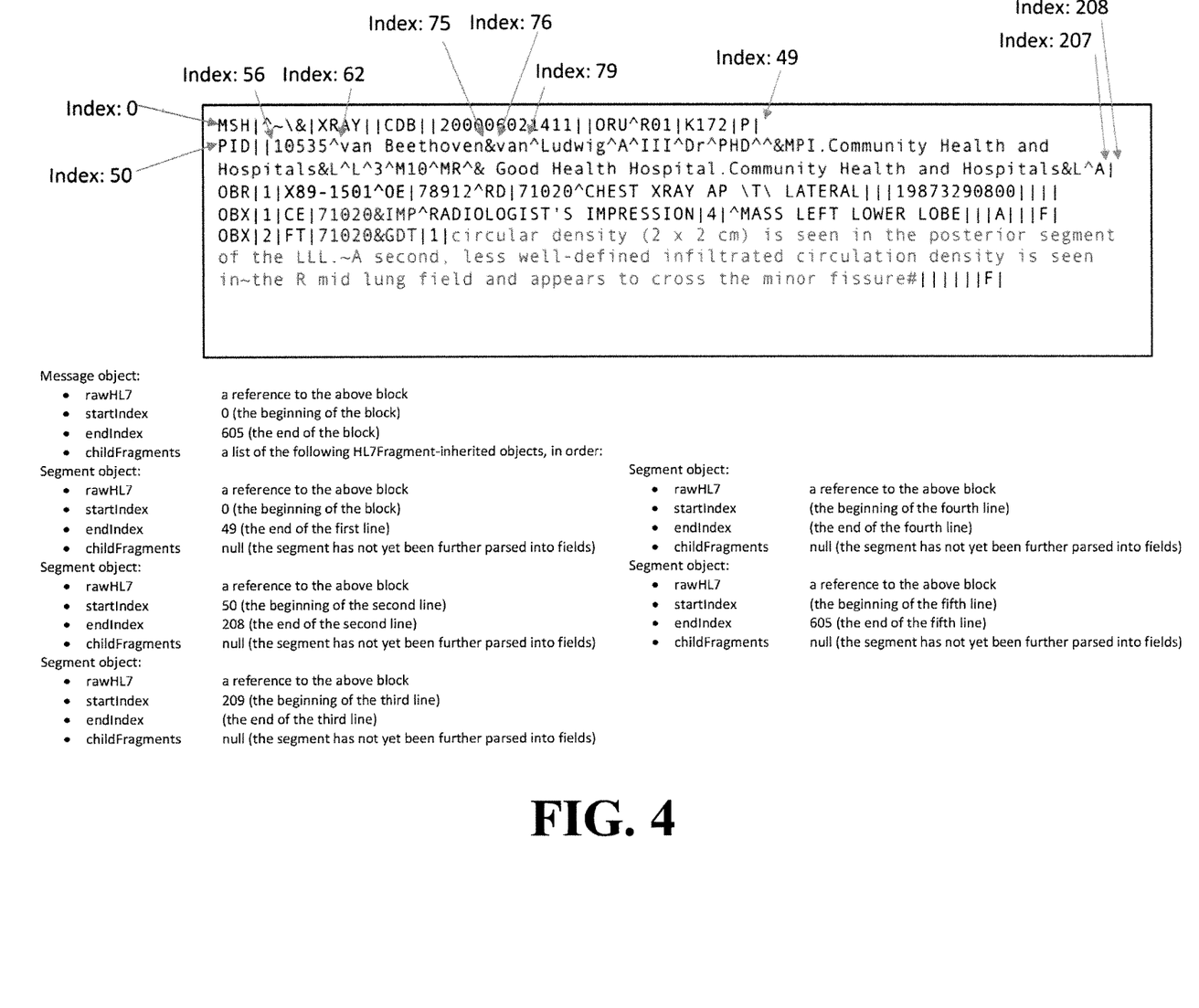
FIG. 4 is an example showing results of applying an initial pass of the flow diagram in FIG. 3 to the sample HL7 message in FIG. 1, in accordance with some embodiments of the disclosure.

The process 300 illustrated in FIG. 3 is explained in reference to the example provided in FIG. 4. FIG. 4 contains the sample HL7 message 100 of FIG. 1. In FIG. 4, the index of some characters have been shown. The entire message, when organized in memory, will have each character associated with an index. When an HL7 message is received, a fragment object called a message object is created. The entire message is viewed as a fragment and the message object populates the following properties: "rawHL7", "startIndex", and "endIndex". "rawHL7" includes a reference to the memory location containing the received HL7 message. "startIndex" includes the index of the beginning of the HL7 message, and in the case of FIG. 4, the "startIndex" is "0". "endIndex" includes the index of the end of the HL7 message, and in the case of FIG. 4, the "endIndex" is "605".

In some embodiments, at this point, the "childFragments" property may be set to null. In other embodiments, the "childFragments" property is populated according to the process 300. Direct children of messages are segments, so in order to populate the "childFragments" property of the message object, process 300 is run to find the segments in the received HL7 message. Segments are then viewed as fragments in FIG. 3. By going through process 300, new fragment objects are created, and in this particular case, segment objects are created.

After starting the process 300 at step 302, Step 304 involves setting character index to the start index of the fragment reference being further divided. In reference to the example of FIG. 4, since segments of the message are the fragments of interest, the character index is set to "0", the index that signifies the start of the first segment. At Step 306, a segment object with "startIndex" set to character index is created. In the example, Step 306 involves "startIndex" set to "0".

At step 308, the process 300 involves checking to see whether the character index points to a delimiter character for the fragment. In the example, since segments are the fragments of interest, the delimiter for segments is the carriage return character 4. In the message of FIG. 4, since character index "0" does not point to a carriage return character, process 300 will proceed to the Step 318, Step 320, and Step 308 loop. These three steps involve incrementing the character index until the carriage return character is found. Step 318 checks to see if there are more characters in the current fragment, and Step 320 increments the character index. Once the carriage return character is found, Step 308 evaluates to Step 310. At Step 310, the "endIndex" of the current segment fragment is set to character index.

At Step 314, the process 300 determines whether there are more characters in the block. If there are no more characters, the process ends, but if there are more characters, then the process returns to Step 306.

Step 322 is a failsafe mechanism in case the fragment being processed is at the end of a message but there is no delimiter at the end of the fragment. "endIndex", as defined, holds an index value beyond the last character, so at Step 322, "endIndex" is set to "character index +1". This is because character index points to a character that is not a delimiter but a character that is part of the HL7 fragment. There may be other definitions of "endIndex", for example, "endIndex" may be defined in other implementations as the last character of the HL7 fragment before the delimiter. Any such variation in the definition of "endIndex" is covered within the scope of the embodiments of the disclosure.

In FIG. 4, after running through process 300, the different segment objects of the sample HL7 message will be populated as provided. The five (5) segment objects correspond to the five (5) segments of the sample HL7 message. Each segment object has a "rawHL7" property which includes a reference to the HL7 message. The "startIndex" and "endIndex" properties of each segment object is populated with their respective indices. The "childFragments" property of each of the segment objects is set to null. At this stage, each segment has not been further parsed into fields.

Figure 5:
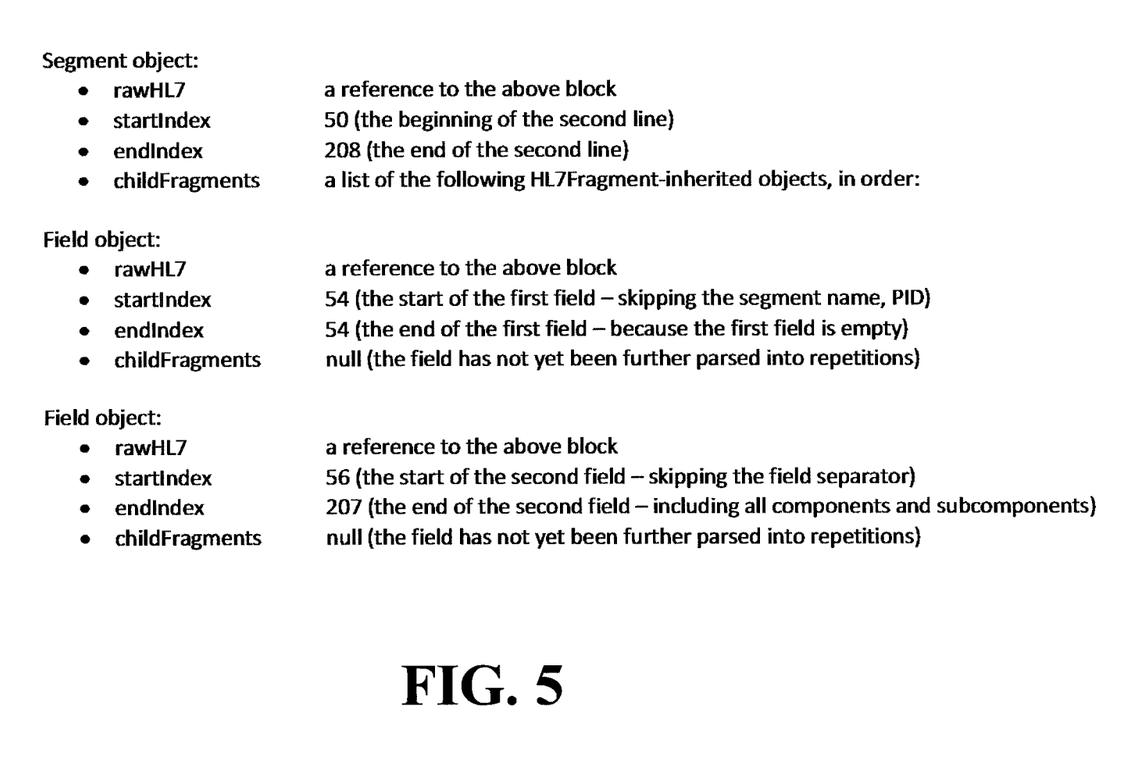
FIG. 5 is an example showing results of creating field objects, in accordance with some embodiments of the disclosure.

As an example, a Rules/Processing Engine 206 receives the sample HL7 message of FIG. 4. The sample message is processed as described with respect to FIG. 3 and FIG. 4. A software client stored in a memory and executed by a processor running on the Rules/Processing Engine 206 requests patient identification information. The software client recognizes that patient identification information is stored in a PID segment and is usually located in the second or third field of the PID segment. The software then requests the value for the second or third field of the PID, and in the case of FIG. 4, the second field of the second segment. Process 300 is then started for segment object pertaining to the PID segment. FIG. 5 provides the segment object of interest (note, this is the second created segment object of FIG. 4).

At Step 304, the character index is set to the "startIndex" of the segment object, which is index_50 in this example. At Step 306, a field object is created with the "startIndex" at "54". In this embodiment, the segment ID, PID, is omitted and is not considered a field of interest. In other embodiments, the segment ID may be considered a field. After determining that "startIndex" is "54", at Step 308, it is determined that the character index at "54" actually points to a field delimiter, the pipe character "|". Step 310 then sets the "endIndex" to "54" as well. Steps 312, 314, and 316 then follow, and a new field object is created since there are more characters in the segment fragment. (Note, the "endIndex" of the PID segment fragment is "208" while character index just incremented from "54" to "56".) The new field object has a "startIndex" of "56", and after going through the process 300, will have an "endIndex" of "207". These two field objects are provided in FIG. 5. At this point, the software client has the value of the second field of the second segment. The information contained in the second field of the second segment is then used by the software client.

In certain embodiments, when a software client requests information, the software client seeks to verify that the information is accurate or valid. In some instances, after obtaining the information, the software client may want to change the value stored in the second field of the second segment. For example, the software client may seek to change the "10535" value in the second field to "10335". The "10535" value is the first component within the second field of the second segment. Process 300 would need to be applied to the obtained second field of the second segment in order to obtain a component object with "startIndex" and "endIndex" for the "10535" value. Once this component object is extracted, the software may create in memory the value "10335" and have the component object "startIndex" and "endIndex" point to the new value in memory. In some embodiments of the disclosure, when a fragment object changes a value from what it had been in the original HL7 message, the "hasChangedChildren" property of the fragment is set to True. By default, after receiving the message and creating segments, the "hasChangedChildren" property is False, and once a change is made to the HL7 message, then the "hasChangedChildren" property is set to "True". Every parent of the changed fragment object will then have their "hasChangedChildren" property set to True.

In another example, after extracting the patient ID "10535" from the first component of the second field of the PID segment, the Rules/Processing Engine 206 finds a record for that patient from the Database 212. In that record are additional patient IDs representing the same patient in different contexts, one of which is to be included in the modified HL7 message to be sent downstream. In some embodiments, the patient ID returned from the database may already be structured as a fully-formatted HL7 fragment string. For this example, suppose the string is as follows: "900443^Beethoven^Ludwig".

The software client in the Rules/Processing Engine 206 then creates a new string of data using the HL7 standard format, to represent the new identifier. This Field object will have a "rawHL7" property that references this newly-created HL7 format string, which is stored separately from the original HL7 message. The Field object will have a "startIndex" of "0" to index the beginning of this new string, and an "endIndex" of "23", just past the end of the new fully-formatted HL7 field string. This new Field can then be added to the end of the PID segment's "childFragments" ordered collection to represent a newly created Field "3" for the PID segment. Thus, a field is created and appended to the PID segment. In this example, the original HL7 message and the newly created field need not be in contiguous locations in memory.

Alternatively, the software client on the Rules/Processing Engine 206 may choose to completely replace the patient identity details, in which case it will simply replace the second or third Field object with the newly-created Field object in the ordered collection of "childFragments" in the PID segment's Segment object. In this case, the Field object that is no longer in the "childFragments" will eventually be "garbage collected", but with a much smaller amount of "garbage" than if it had contained an entire copy of the string data from the original HL7 message. In either of these scenarios, the Segment object representing the PID segment would have its "hasChangedChildren" property set to true so that future rendering of the PID segment will use the new Field object to emit its data.

In some embodiments, if the software client on the Rules/Processing Engine later needs to isolate one of the components of the new field, the same splitting logic will occur, and every child fragment of that field will have its "rawHL7" property reference the same "900443^Beethoven^Ludwig" string already in RAM.

Figure 6:
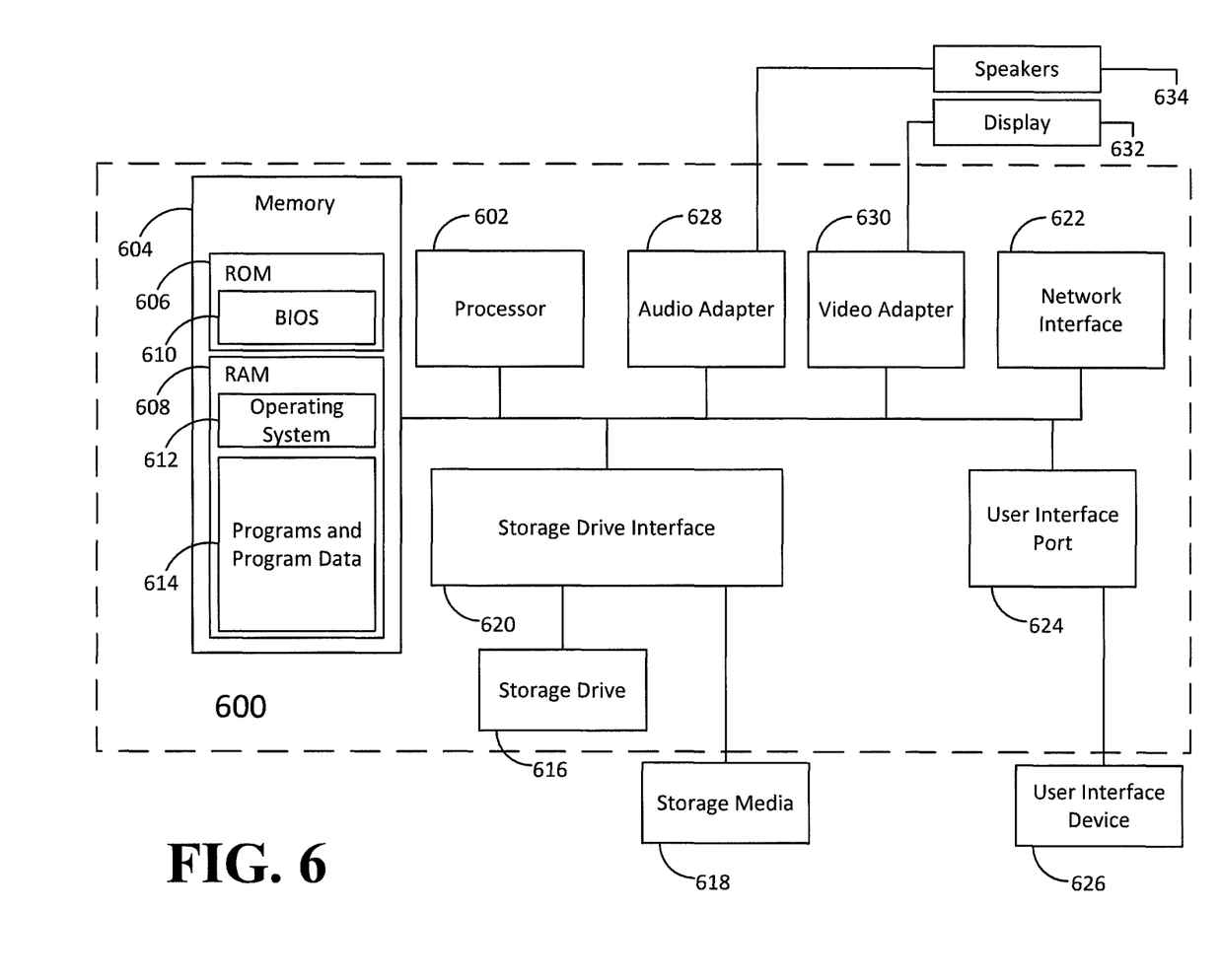
FIG. 6 is a block diagram illustrating an example computer environment in which the process of identifying HL7 message features may be performed.

FIG. 6 is a block diagram illustrating an example of a computing environment in which the process of identifying HL7 message features may be performed. The computing environment may also house certain embodiments of the disclosure that minimize garbage collection in HL7 manipulation. Those of ordinary skill in the art will understand that the meaning of the term "computer" or "computing" as used in the examples is not limited to a personal computer but may also include other microprocessor or micro-controller based systems. For example, embodiments of the disclosure may be implemented on mainframes, servers, internet appliances, microprocessor based or programmable consumer electronics, multi-processor systems, tablet computers, etc.

The computing environment may include a computer 600, which includes a processor 602, memory 604, and a system bus to facilitate communication between different units of computer 600. The memory 604 may include a read only memory (ROM) 606 and a random access memory (RAM) 608. In some embodiments, the ROM 606 stores basic input/output system (BIOS) 610, which contains basic routines that assist in information exchange between different units within the computer 600. The RAM 608 is working memory and may store a variety of items including parts of the operating system 612, and programs and data necessary for correct operation of these programs 614. The computer 600 may include a storage device 616 with a higher capacity than RAM 608. Storage device 616 may be multiple hard disk drives (HDDs), solid state drives (SSDs), magnetic disk drives, hybrid drives, optical disk drive, etc. Computer 600 may interface removable drives or storage media 618 which may include flash drives, optical media, etc. Storage Drive Interface 620 interfaces internal and external storage options with the system bus. HL7 messages, stored in Storage device 616, may be read into RAM 608.

A user may enter commands and information into computer 600 through user interface device 626. User interface device 626 includes a microphone, a touch screen, a touchpad, a keyboard, a mouse, a joystick, and a stylus. User Interface Port 624 interfaces the User Interface Device 626 with the system bus. The port 624 may include a serial port, a parallel port, a universal serial bus (USB), a game port, a proprietary port, a 1394 port, a microphone port, etc. Computer 600 may further include one or more network interfaces 622 to provide network connectivity with one or more devices. Network interface 622 may be a wired or wireless network interface, supporting several wireless technologies including Bluetooth®, Wi-Fi, ultra-wide band (UWB), wireless USB, ZigBee, WiMAX, long term evolution (LTE), etc. HL7 messages may be obtained at network interface 622 and subsequently stored in RAM 608 or storage device 616. Lastly, computer 600 may interface with input and output devices. In FIG. 6, audio adapter 628 and video adapter 630 provide connections to a speaker 634 and display 632, respectively.

Embodiments of the disclosure provide a method of using indices to mark fragments of an HL7 message. When a software client is working with the HL7 message, the software client may change the original message by modifying certain values in the fragments of interest and updating the indices of the fragments accordingly. This method works directly with the original HL7 message and thus, avoids making multiple copies of the HL7 message. By adopting certain aspects of the disclosure, a software system may manipulate HL7 messages without consuming too much RAM or necessitating the need for a computer to spend a long amount of time in "garbage collection". In conventional approaches, unnecessary pressure is placed on computer runtime system since HL7 message processing may involve multiple copies of values within the hierarchy stored in memory. As such, computer resources would be diverted to garbage collection where no-longer-used memory blocks are rearranged and cleaned up so that they become available for future productive work. During "garbage collection" time, the throughput of an HL7 message processing system is significantly reduced. In some instances, the throughput is measured in terms of number of HL7 messages processed per second. Embodiments of the disclosure provide an efficient means of HL7 message processing, allowing throughput to remain high. Accordingly, embodiments of the disclosure provide systems and method that improve the functioning of the computer itself by reducing and streamlining memory usage.

Embodiments of the disclosure allow preserving the original relative positions within the original message of a field, repetition, component, or subcomponent when its value is copied or moved from one location in the inbound HL7 message to a different position in the outbound HL7 message, rather than creating another copy of the data contained within that field, repetition, component, or subcomponent.

Embodiments of the disclosure allow accepting modifications of data values in the HL7 message, assigning a new value to an element at any layer of the hierarchy, holding a single copy of the entire new value, and interpreting the values of individual data elements within that hierarchy in terms of their relative positions within that single copy of the new value. Thus, avoiding copying the values of those data elements into the hierarchical object model, and avoiding making any modifications to the area of RAM containing the original message.

Furthermore, the disclosure provides additional embodiments on manipulation of HL7 messages, particularly moving/copying values, populating new values, and tracking changes that have been made to an HL7 message. In one example, the software client on the Rules/Processing Engine 206 may move or copy a value from one segment to another segment, or from one part of the HL7 message hierarchy to another. With a move or copy, a source fragment is identified, and a destination parent is also identified. A new HL7 fragment object of the appropriate type is created to represent the destination field, repetition, component, or subcomponent. Since the original value for this new destination is being copied or moved from somewhere else in the original message, the new HL7 fragment object's "rawHL7" value continues to reference the original HL7 message, and the new HL7 fragment object's "startIndex" and "endIndex" represent the starting and ending locations, respectively, for the portion of that HL7 message that holds the desired value for the destination HL7 fragment.

In another example, the software client on the Rules/Processing Engine 206 may populate a fragment of an HL7 message with a value provided by an external source. A new HL7 fragment object is created to represent a destination field, repetition, component, or subcomponent. The "rawHL7" value of the new fragment object is set to reference a new value provided by the external source, and the "startIndex" and "endIndex" are set to reference the beginning and end of the new value. If the newly created HL7 fragment is later parsed to populate its child fragments collection, the newly created child fragments will have their "rawHL7" values set to reference the same external value as is referenced by their parent HL7 fragment object, and their startIndex and endIndex values will be set relative to the block of memory holding that external value.

In yet another example, embodiments of the disclosure when incorporated in a computing device, for example, on the Rules/Processing Engine 206, may track changes made to an HL7 message by monitoring values of "hasChangedChildren" properties of HL7 fragment objects. Whenever a member of an HL7 fragment object's childFragments is changed, the "hasChangedChildren" property of the parent HL7 fragment is set to "true", and the "true" value cascades all the way up the hierarchy from that parent to its parent until it reaches an HL7 fragment whose parent is null, i.e., the HL7 message object.

Compared to conventional approaches for parsing HL7 messages, embodiments of the disclosure consistently perform better. After testing several different characteristics of real-world HL7 messages in multiple batch sizes, performance improvements ranged from a 5% improvement to a 75% improvement. The average improvement in the number of messages processed per second was approximately 20%. These quoted improvements are realized without making any performance improvements to the domain-specific I/O, analysis, and/or processing that the external software client does in-between requests to the HL7 library used for the message parsing.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for processing Health Level-7 (HL7) messages, comprising:
   receiving, over an electronic data network, an HL7 message and storing the HL7 message in a memory as a stored HL7 message;
   creating a data structure representation of the stored HL7 message in the memory that stores a start index of the stored HL7 message and an end index of the stored HL7 message, wherein the start index of the stored HL7 message indicates a beginning of the stored HL7 message and the end index of the stored HL7 message indicates an end of the stored HL7 message;
   hierarchically creating, in the memory, from the data structure representation of the stored HL7 message, a first data structure representation of a fragment in the stored HL7 message, the first data structure representation of the fragment including a start index and an end index corresponding to the fragment in the stored HL7 message; and
   modifying the stored HL7 message by appending a second data structure representation of the fragment to a child list associated with a parent of the fragment, wherein the second data structure representation of the fragment includes a start index and an end index of a storage location storing an updated value of the fragment.

2. The method according to claim 1, wherein:
   the stored HL7 message is organized in a hierarchical manner, the stored HL7 message comprising segments, the segments comprising fields, the fields comprising repetitions, the repetitions comprising components, and the components comprising subcomponents; and
   types of fragments in the stored HL7 message are selected from a group consisting of: (a) a message fragment (b) a segment fragment, (c) a field fragment, (d) a repetition fragment, (e) a component fragment, and (f) a subcomponent fragment.

3. The method according to claim 2, wherein:
   the stored HL7 message comprises delimiters for each fragment, wherein a different delimiter is used for each type of fragment in the stored HL7 message.

4. The method according to claim 2, wherein:
   the end index of the fragment in the stored HL7 message is an index of the stored HL7 message containing a delimiter.

5. The method according to claim 2, wherein:
   the first data structure representation created hierarchically further stores information selected from a group consisting of: (a) information on a hierarchical relationship between the fragment and another fragment indicating a parent relationship, a child relationship, or both, and (b) information on whether a value related to a child fragment has changed.

6. The method according to claim 5, wherein:
   the first data structure representation created hierarchically further stores information selected from a group consisting of: (a) information indicating whether a segment is a required segment, (b) information indicating whether the segment is a ghost parent, the ghost parent signifying that the segment was created for a child segment without a parent, and (c) information indicating a list of child segments.

7. The method according to claim 1, wherein modifying the stored HL7 message comprises one or more of:
   extracting information from the stored HL7 message between the start index and the end index of the fragment in the stored HL7 message;
   moving a value from one part of the stored HL7 message to another, the value located between the start index and the end index of the fragment in the stored HL7 message;
   copying a value from one part of the stored HL7 message to another, the value located between the start index and the end index of the fragment in the stored HL7 message;
   populating a new value in the stored HL7 message to replace a value located between the start index and the end index of the fragment in the stored HL7 message; and
   tracking changes that have been made to the stored HL7 message between the start index and the end index of the fragment in the stored HL7 message.

8. The method according to claim 1, wherein modifying the stored HL7 message results in an HL7 message with fragments stored in non-contiguous locations in the memory.

9. A computing device for processing Health Level-7 (HL7) messages, the computing device comprising a processor and a memory with instructions stored thereon, such that when the processor executes the instructions, the computing device is configured to:
   receive, over an electronic data network, an HL7 message and store the HL7 message in the memory as a stored HL7 message;
   hierarchically create, in the memory, a first data structure representation of a fragment in the stored HL7 message, the first data structure representation of the fragment including a start index and an end index of the fragment in the stored HL7 message,
      wherein the stored HL7 message comprises fragments organized by type in a hierarchical manner, and
      wherein the hierarchical manner indicates that the stored HL7 message comprises one or more segments, each segment comprising one or more fields, each field comprising one or more repetitions, each repetition comprising one or more components, and each component comprising one or more subcomponents; and
   modify the stored HL7 message by appending a second data structure representation of the fragment to a child list associated with a parent of the fragment, wherein the second data structure representation of the fragment includes a start index and an end index of a storage location storing an updated value of the fragment.

10. The computing device according to claim 9, wherein:
    the stored HL7 message comprises delimiters for each fragment, wherein a different delimiter is used for each type of fragment in the stored HL7 message.

11. The computing device according to claim 10, wherein:
    the end index of the fragment in the stored HL7 message is an index of the stored HL7 message containing a delimiter.

12. The computing device according to claim 9, wherein:
    the first data structure representation created hierarchically further stores information selected from a group consisting of: (a) information on a hierarchical relationship between the fragment and another fragment indicating a parent relationship, (b) information on a hierarchical relationship between the fragment and another fragment indicating a child relationship, and (c) information on whether a value related to a child fragment has changed.

13. The computing device according to claim 12, wherein: the first data structure representation created hierarchically further stores information selected from a group consisting of: (a) information indicating whether a segment is a required segment, (b) information indicating whether the segment is a ghost parent, the ghost parent signifying that the segment was created for a child segment without a parent, and (c) information indicating a list of child segments.

14. The computing device according to claim 9, wherein modifying the stored HL7 message comprises one or more of:
    extracting information from the stored HL7 message between the start index and the end index of the fragment in the stored HL7 message;
    moving a value from one part of the stored HL7 message to another, the value located between the start index and the end index of the fragment in the stored HL7 message;
    copying a value from one part of the stored HL7 message to another, the value located between the start index and the end index of the fragment in the stored HL7 message;
    populating a new value in the stored HL7 message to replace a value located between the start index and the end index of the fragment in the stored HL7 message; and
    tracking changes that have been made to the stored HL7 message between the start index and the end index of the fragment in the stored HL7 message.

15. A non-transitory computer readable medium for processing Health Level-7 (HL7) messages, the non-transitory computer readable medium containing program instructions that causes a computer to perform a method comprising:
    receiving, over an electronic data network, an HL7 message and storing the HL7 message in a memory as a stored HL7 message;
    hierarchically creating, in the memory, a first data structure representation of a fragment in the stored HL7 message, the first data structure representation of the fragment including a start index and an end index of the fragment in the stored HL7 message,
        wherein the start index indicates a beginning of the fragment and the end index indicates an end of the fragment,
        wherein the stored HL7 message comprises fragments organized by type in a hierarchical manner, and
        wherein the hierarchical manner indicates that the stored HL7 message comprises one or more segments, each segment comprising one or more fields, each field comprising one or more repetitions, each repetition comprising one or more components, and each component comprising one or more subcomponents; and
    modifying the stored HL7 message by appending a second data structure representation of the fragment to a child list associated with a parent of the fragment, wherein the second data structure representation of the fragment includes a start index and an end index of a storage location storing an updated value of the fragment.

16. The non-transitory computer readable medium according to claim 15, wherein:
    the stored HL7 message comprises delimiters for each fragment, wherein a different delimiter is used for each type of fragment in the stored HL7 message.

17. The non-transitory computer readable medium according to claim 16, wherein:
    the end index is an index of the stored HL7 message containing a delimiter.

18. The non-transitory computer readable medium according to claim 15, wherein:
    the first data structure representation created hierarchically further stores information selected from a group consisting of: (a) information on a hierarchical relationship between the fragment and another fragment indicating a parent relationship, (b) information on a hierarchical relationship between the fragment and another fragment indicating a child relationship, and (c) information on whether a value related to a child fragment has changed.

19. The non-transitory computer readable medium according to claim 18, wherein:
    the first data structure representation created hierarchically further stores information selected from a group consisting of: (a) information indicating whether a segment is a required segment, (b) information indicating whether the segment is a ghost parent, the ghost parent signifying that the segment was created for a child segment without a parent, and (c) information indicating a list of child segments.

20. The non-transitory computer readable medium according to claim 15, wherein modifying the stored HL7 message comprises one or more of:
    extracting information from the stored HL7 message between the start index and the end index of the fragment in the stored HL7 message;
    moving a value from one part of the stored HL7 message to another, the value located between the start index and the end index of the fragment in the stored HL7 message;
    copying a value from one part of the stored HL7 message to another, the value located between the start index and the end index of the fragment in the stored HL7 message;
    populating a new value in the stored HL7 message to replace a value located between the start index and the end index of the fragment in the stored HL7 message; and
    tracking changes that have been made to the stored HL7 message between the start index and the end index of the fragment in the stored HL7 message.

* * * * *